(12) United States Patent
Holman et al.

(10) Patent No.: US 8,398,697 B2
(45) Date of Patent: Mar. 19, 2013

(54) BIFURCATION CATHETER ASSEMBLY WITH DISTALLY MOUNTED SIDE BALLOON AND METHODS

(75) Inventors: Tom Holman, Minneapolis, MN (US); Zach Tegels, Otsego, MN (US); Adam Jennings, Buffalo, MN (US); Kathy Prindle, Robbinsdale, MN (US); Mary Bronson, Elk River, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1270 days.

(21) Appl. No.: 12/139,209

(22) Filed: Jun. 13, 2008

(65) Prior Publication Data
US 2009/0312702 A1 Dec. 17, 2009

(51) Int. Cl.
*A61F 2/06* (2006.01)
(52) U.S. Cl. ................. 623/1.11; 623/1.35
(58) Field of Classification Search ........ 623/1.11–1.54; 606/191–198; 604/103.01–103.07
See application file for complete search history.

(56) References Cited

U.S. PATENT DOCUMENTS

| | | | |
|---|---|---|---|
| 6,129,738 A * | 10/2000 | Lashinski et al. ........... 606/194 |
| 6,146,356 A | 11/2000 | Wang et al. | |
| 6,210,429 B1 | 4/2001 | Vardi et al. | |
| 6,325,826 B1 | 12/2001 | Vardi et al. | |
| 6,780,199 B2 * | 8/2004 | Solar et al. ........... 623/1.11 |
| 7,220,275 B2 | 5/2007 | Davidson et al. | |
| 7,344,557 B2 * | 3/2008 | Yadin ........... 623/1.11 |
| 7,655,030 B2 * | 2/2010 | Williams et al. ........... 623/1.11 |
| 7,871,396 B2 * | 1/2011 | Jennings et al. ........... 604/101.01 |
| 2005/0015108 A1 | 1/2005 | Williams et al. | |
| 2007/0100301 A1 | 5/2007 | Gumm | |
| 2007/0203562 A1 * | 8/2007 | Malewicz et al. ........... 623/1.11 |
| 2008/0086191 A1 | 4/2008 | Valencia et al. | |
| 2009/0036830 A1 | 2/2009 | Jablonski et al. | |

FOREIGN PATENT DOCUMENTS
WO 2008144311 11/2008
* cited by examiner

*Primary Examiner* — Gary Jackson
*Assistant Examiner* — Kendra Obu
(74) *Attorney, Agent, or Firm* — Seager, Tufte & Wickhem, LLC

(57) ABSTRACT

A catheter assembly and related methods directed to a main balloon and a side balloon, wherein the side balloon is coupled in fluid communication with the main balloon at a location distal of the side balloon. In one example, a side inflation member couples the side balloon in fluid communication to the main balloon at a distal end portion of the main balloon. A side catheter branch of the catheter assembly, which defines a side guidewire lumen, can be operatively mounted to the side balloon at a side balloon connection point to help maintain alignment of the side catheter branch relative to the side balloon.

16 Claims, 5 Drawing Sheets

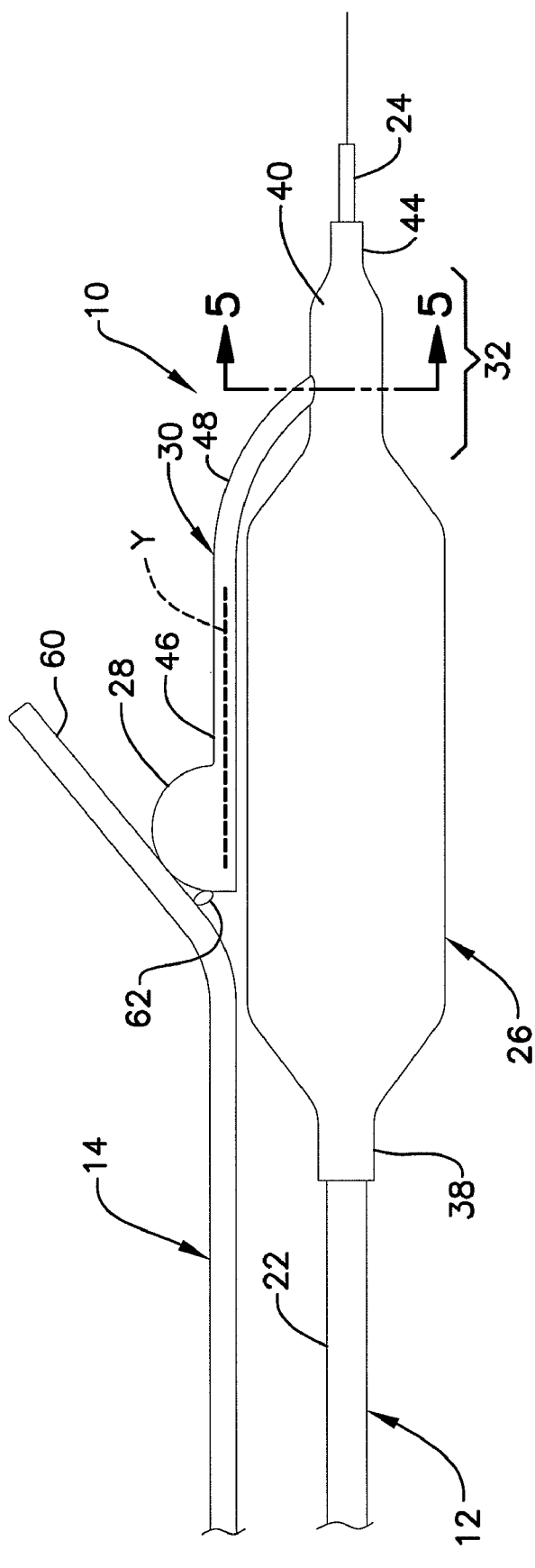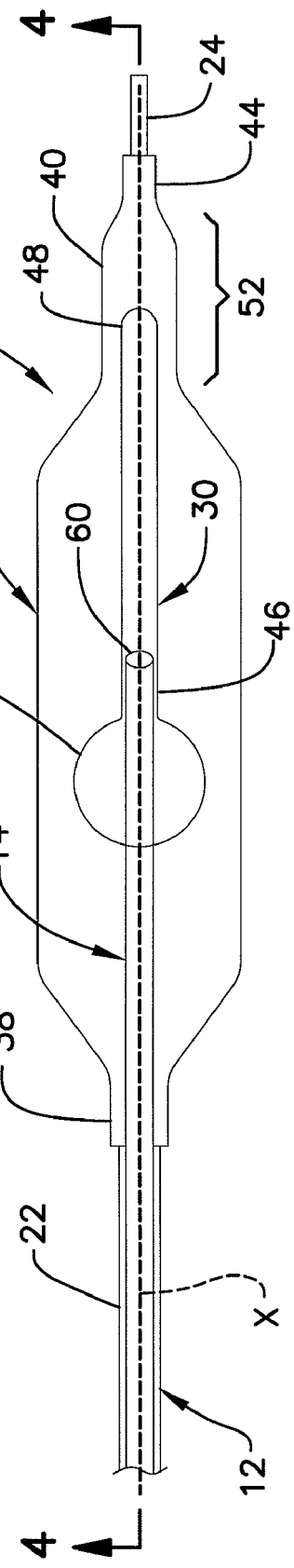

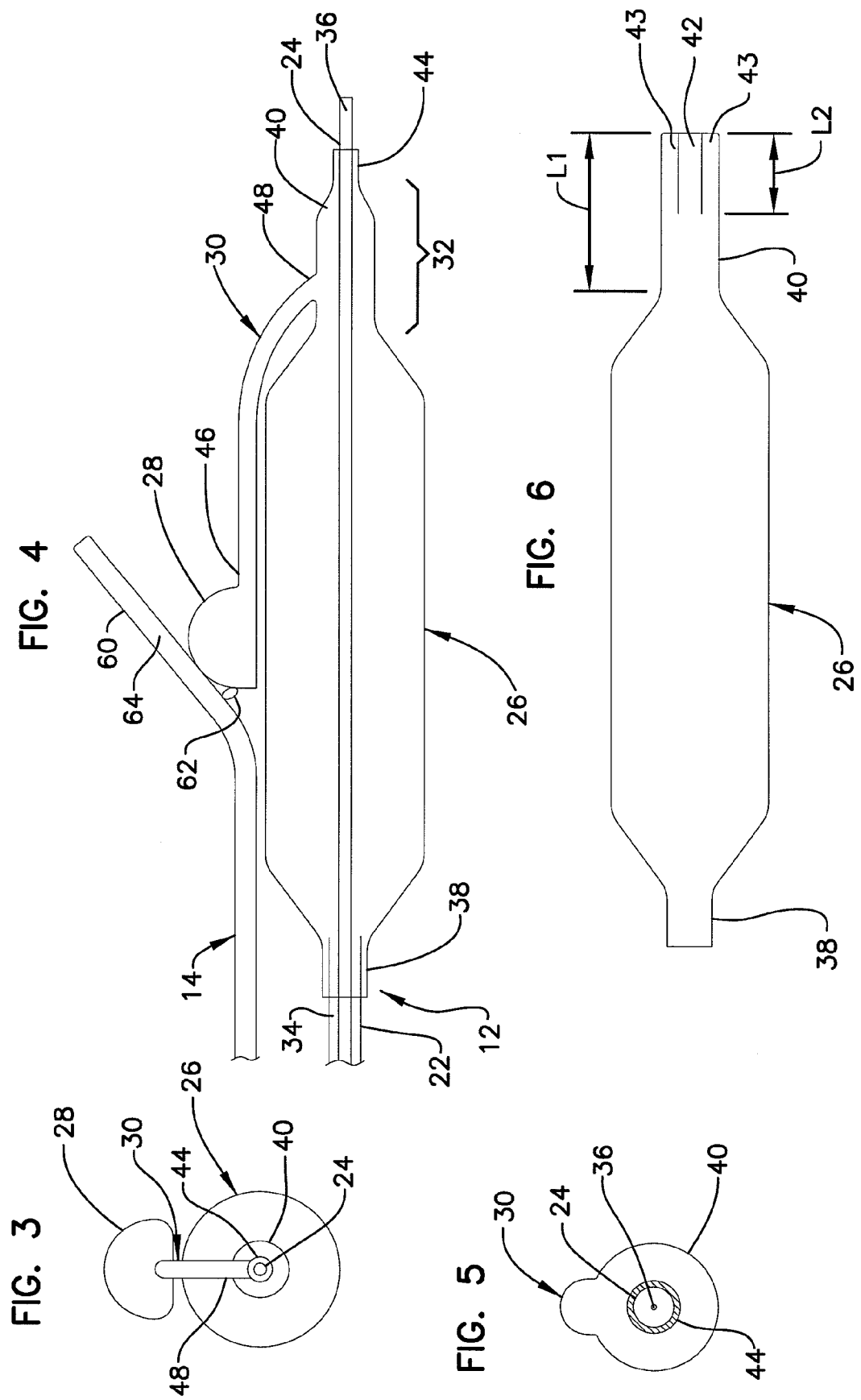

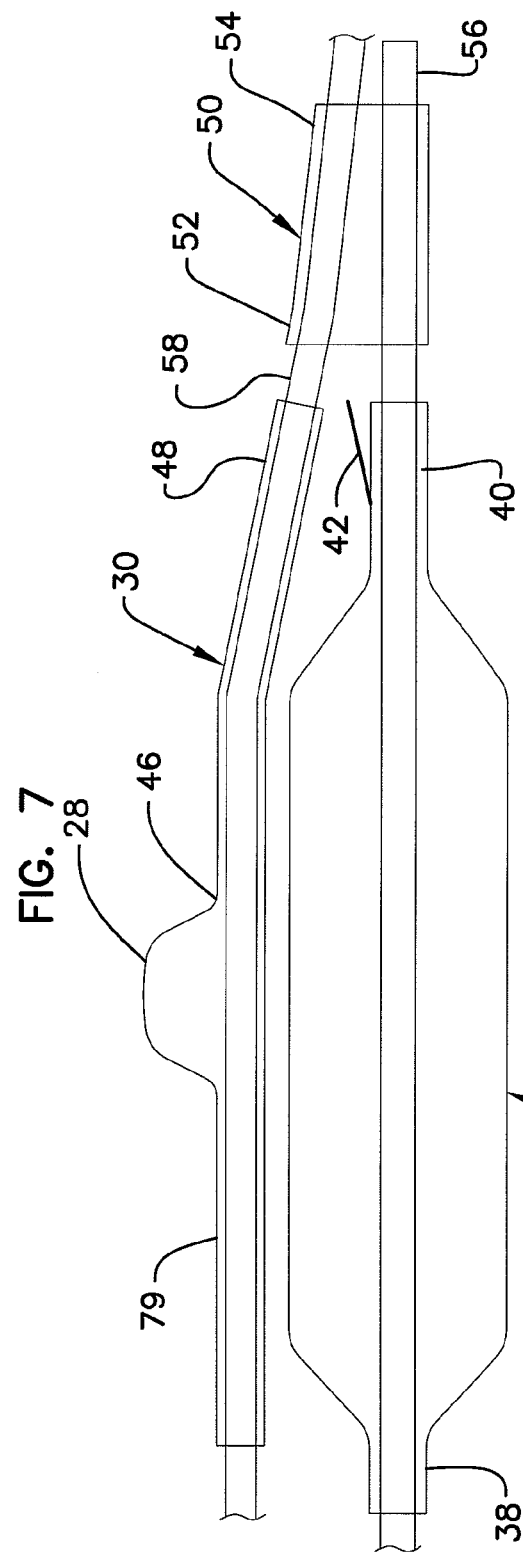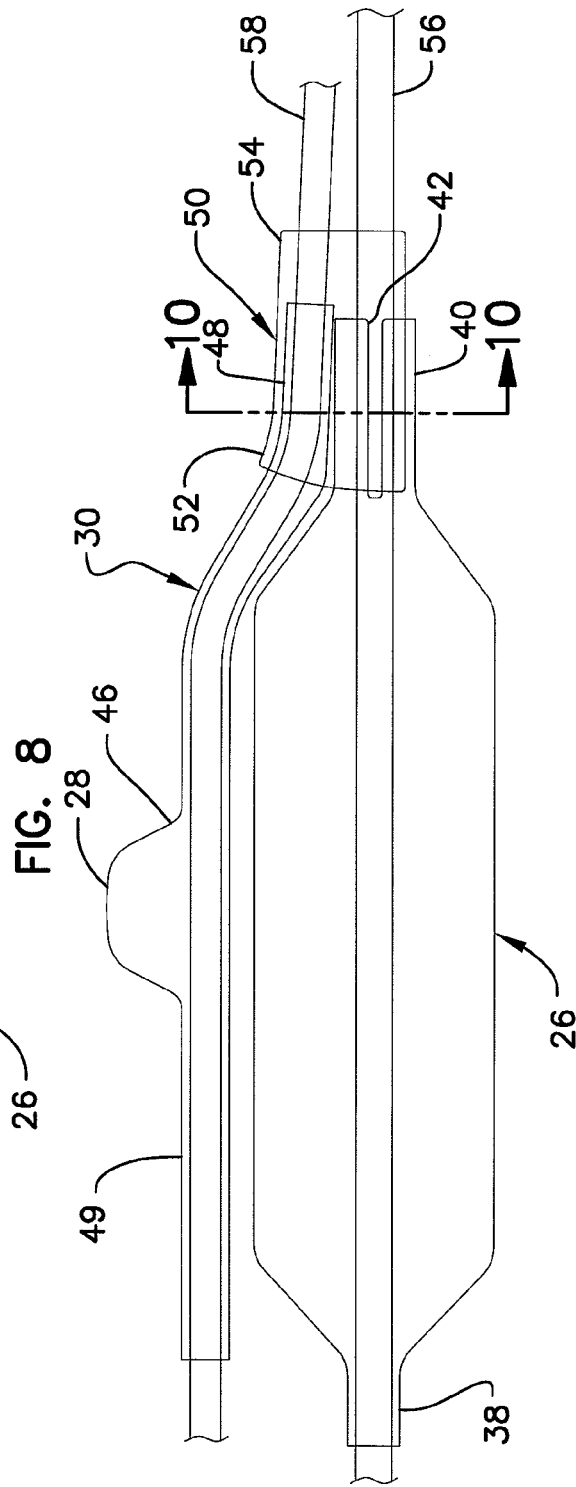

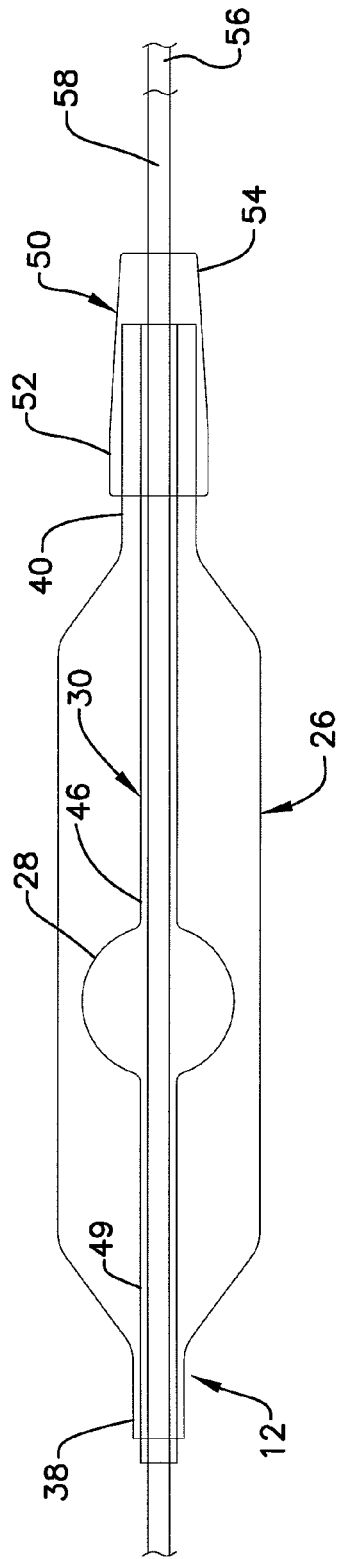
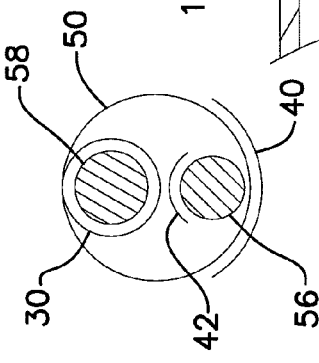
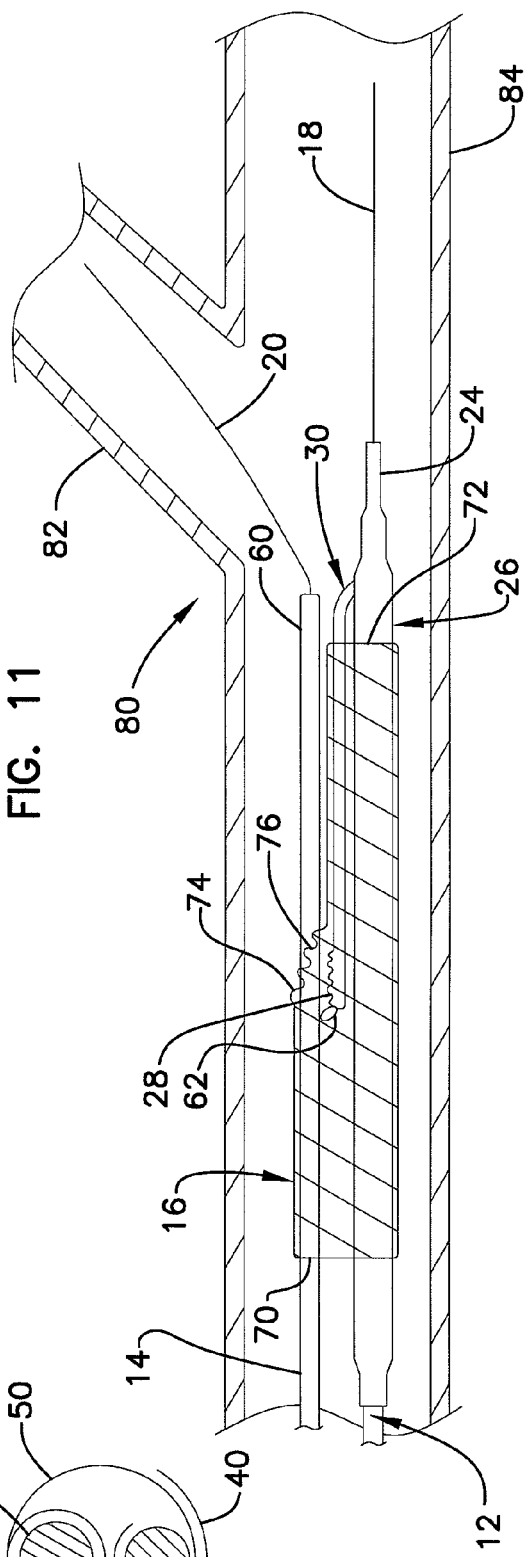
FIG. 9
FIG. 10
FIG. 11

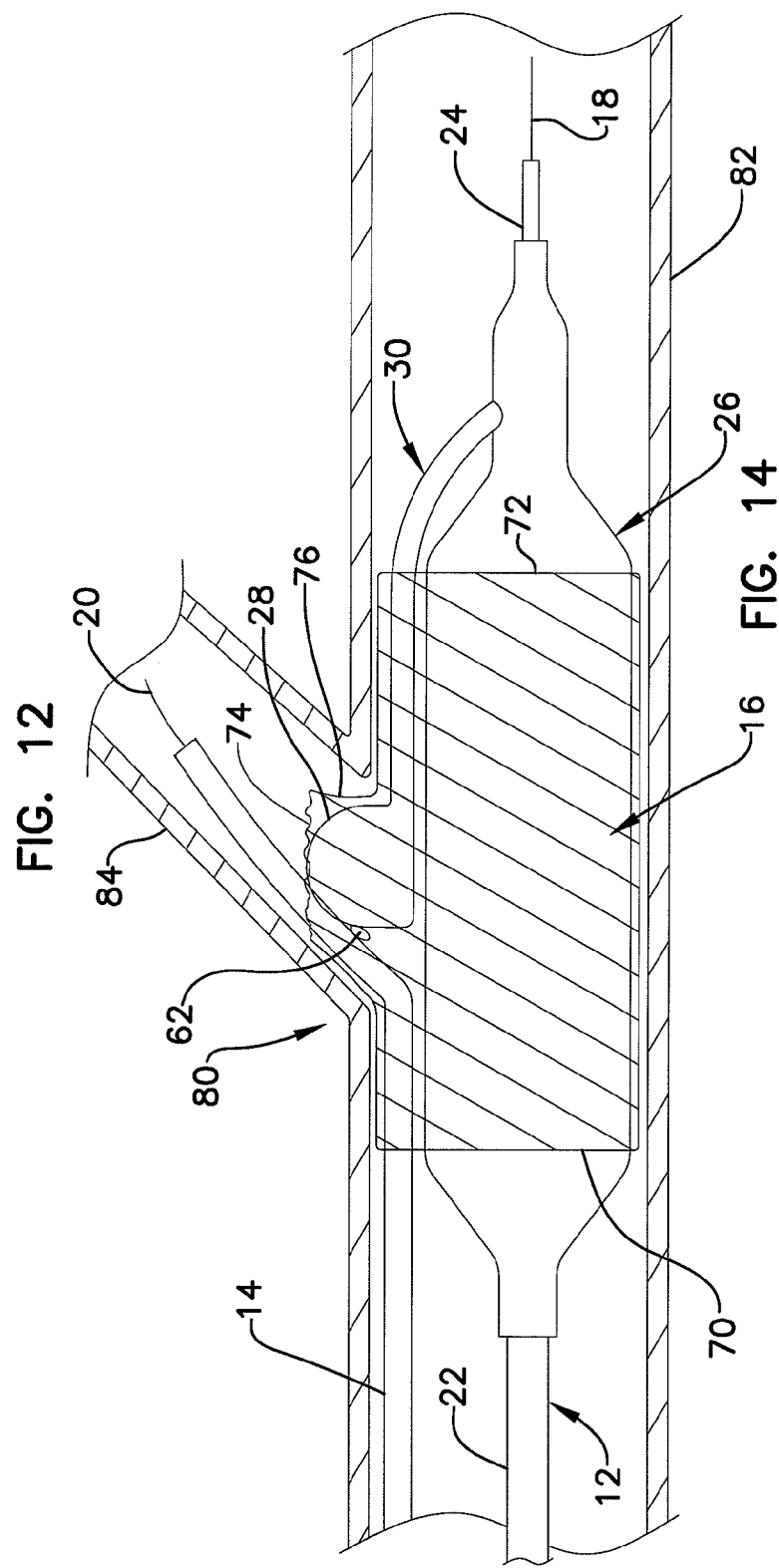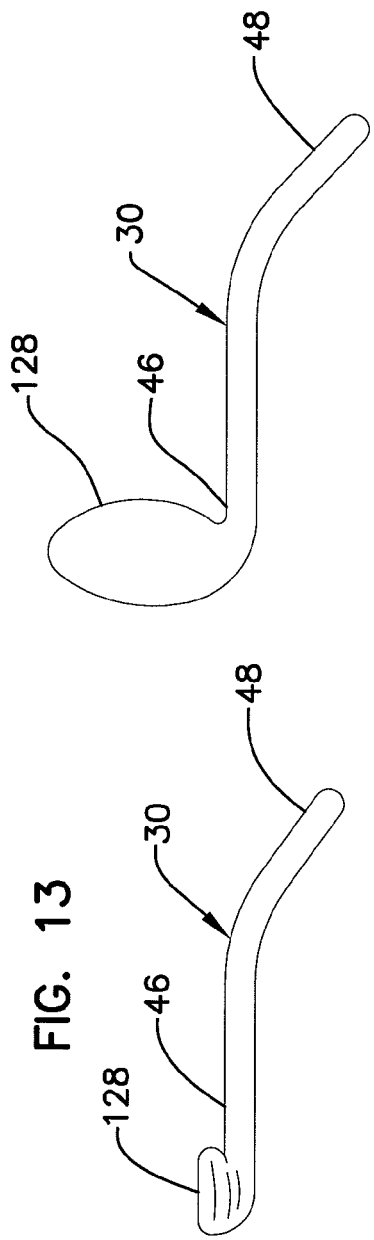

BIFURCATION CATHETER ASSEMBLY WITH DISTALLY MOUNTED SIDE BALLOON AND METHODS

TECHNICAL FIELD

This disclosure relates to catheter assemblies configured for treatment of a vessel bifurcation. Preferred arrangements provide for side balloon attachment distal of the main balloon.

BACKGROUND

Catheters are used with stents and inflatable structures to treat conditions such as strictures, stenoses, and narrowing in various parts of the body. Various catheter designs have been developed for the dilatation of stenoses and to deliver and deploy stents at treatment sites within the body.

Stents are typically intraluminally placed by a catheter within a vein, artery, or other tubular shaped body organ for treating conditions such as, for example, occlusions, stenoses, aneurysms, dissections, or weakened, diseased, or abnormally dilated vessels or vessel walls, by expanding the vessels or by reinforcing the vessel walls. Once delivered, the stents can be expanded using one or more inflatable members such as balloons. Stents can improve angioplasty results by preventing elastic recoil and remodeling of the vessel wall and treating dissections in blood vessel walls caused by balloon angioplasty of coronary arteries. Stents can also be used as a drug delivery medium for treatment of damaged portions of a vessel.

While conventional stent technology is relatively well developed, stent technologies related to treatment of the region of a vessel bifurcation are still being developed. One challenge related to treatment of a vessel bifurcation involves minimizing the outer profile of the catheter assembly thereby improving the ease in advancing the catheter assembly to the vessel bifurcation.

SUMMARY OF THE DISCLOSURE

The present disclosure relates to catheter assemblies having a main balloon and a side balloon. The side balloon is positioned along a length of the main balloon and is configured to extend in a radially outward direction relative to the main balloon when inflated. The side balloon is coupled in fluid communication with the main balloon at a location distal of the side balloon. In one example, a side inflation member is coupled in fluid communication at a proximal end thereof with the side balloon, and is coupled in fluid communication at a distal end thereof to the main balloon at a distal end portion of the main balloon.

The present application also relates to a catheter assembly having a main catheter branch that includes a main balloon and a side balloon, and a side catheter branch that is operatively mounted to the side balloon. The side catheter branch defines a side guidewire lumen. A separate main guidewire lumen extends through the main catheter branch. Mounting the side catheter branch to the side balloon can help maintain alignment of the side catheter branch relative to the side balloon and a lateral branch opening of a stent operative mounted to the catheter assembly, wherein the side balloon is radially and axially aligned with the lateral branch opening.

There is no requirement that an arrangement include all features characterized herein to obtain some advantage according to this disclosure.

BRIEF DESCRIPTION OF THE DRAWINGS

FIG. 1 is a schematic side view of a catheter assembly constructed according to principles of this disclosure.

FIG. 2 is a schematic top view of the catheter assembly of FIG. 1.

FIG. 3 is a schematic end view of the catheter assembly of FIG. 1.

FIG. 4 is a schematic cross-sectional side view of the catheter assembly of FIG. 2 taken along cross-sectional indicators 4-4.

FIG. 5 is a schematic cross-sectional end view of the catheter assembly of FIG. 1 taken along cross-sectional indicators 5-5.

FIG. 6 is a schematic top view of the main balloon of FIG. 1.

FIG. 7 is a schematic side view of the catheter assembly of FIG. 1 with the proximal bond components in a partially disassembled state.

FIG. 8 is a schematic side view of the catheter assembly of FIG. 7 with the proximal bond components in an assembled, but unbonded state.

FIG. 9 is a schematic top view of the catheter assembly of FIG. 8.

FIG. 10 is a schematic cross-sectional end view of the catheter assembly of FIG. 8 taken along cross-sectional indicators 10-10.

FIG. 11 is a schematic side view of the catheter assembly of FIG. 1 with a stent carried thereon, the balloons in a deflated state, and positioned at a vessel bifurcation.

FIG. 12 is a schematic side view of the catheter assembly of FIG. 11 with the balloons in an inflated state at the vessel bifurcation.

FIG. 13 is a schematic side view of another example side balloon in a deflated state according to principles of this disclosure.

FIG. 14 is a schematic side view of the side balloon shown in FIG. 13 in an inflated state.

DETAILED DESCRIPTION

General Background

This disclosure relates to bifurcation treatment systems, catheter assemblies, and related methods of treating bifurcations in a patient's body. The term bifurcation means a division location from one unit into two or more units. Generally, two types of bifurcations of a body organ include: 1) a main tubular member defining a main lumen and a branch tubular member defining a branch lumen that extends or branches off from the main tubular member, wherein the main and branch lumens are in fluid communication with each other, and 2) a primary or main member defining a primary or main lumen (also referred to as a parent lumen) that splits into first and second branch members defining first and second branch lumens. The term lumen means the cavity or bore of a tubular structure such as a tubular organ (e.g., a blood vessel).

An example bifurcation is a vessel bifurcation that includes a continuous main vessel and a branch vessel, wherein the vessels define a main lumen and a branch lumen, respectively that are in fluid communication with each other. Alternatively, a vessel bifurcation can include a parent vessel that divides into first and second branch vessels, wherein the vessels define a parent lumen and first and second branch lumens, respectively, which lumens are all in fluid communication with each other.

Example applications of the inventive principles disclosed herein include cardiac, coronary, renal, peripheral vascular, gastrointestinal, pulmonary, urinary, and neurovascular systems. The catheter assemblies, systems and methods disclosed herein can be used for locating a branch vessel of the vessel bifurcation and for placement of a stent relative to the vessel bifurcation for treatment of the vessel bifurcation.

While alternatives are possible, the example catheter assemblies disclosed herein generally include at a distal end portion thereof at least a main catheter branch and a side catheter branch. The side catheter branch typically includes a side guidewire housing that defines a side guidewire lumen. A distal end portion of the side catheter branch is configured to extend into a branch vessel at a vessel bifurcation. The side catheter branch is used to align features of a stent carried by the proximal end portion of the vessel bifurcation treatment system with an ostium (also referred to as a branch vessel opening) into the branch vessel.

The main catheter branch usually includes a catheter shaft having a distal end portion. A main balloon and a side balloon are positioned at the distal end portion of the catheter shaft. The main catheter branch can also include a main guidewire housing that defines a main guidewire lumen. The main balloon is positioned along a length of a portion of the main guidewire housing. The side balloon is positioned on a side inflation member. The side inflation member typically extends parallel with the main balloon. The side inflation member defines a side inflation lumen. The side inflation member includes at least a distal segment that is connected in fluid communication with the side balloon. The side inflation member can also include a proximal segment. The proximal segment can be connected in fluid communication with the side balloon. The side and main balloons can be connected in fluid communication with the same source of inflation fluid.

One aspect of the present disclosure relates to connecting the side inflation lumen in fluid communication with the main balloon at a distal end portion of the main balloon that is located distal of the side balloon. A distal end portion of the main balloon can include a distal waist of the main balloon. Another aspect of the present disclosure relates to a physical connection of the side balloon to the side catheter branch. This connection can help maintain alignment of the side balloon and the lateral branch opening of the stent relative to the branch vessel. A further aspect of the present disclosure relates to a distal bond arrangement of the main balloon and side inflation member and related methods of assembly and manufacture.

The Example of FIGS. 1-12

Referring now to FIGS. 1-12 an example catheter assembly 10 is shown and described. The catheter assembly 10 includes a main catheter branch 12, a side catheter branch 14, and a stent 16. The main catheter branch 12 includes a catheter shaft 22, a main guidewire housing 24, a main balloon 26, a side balloon 28, and a side inflation member 30. The side catheter branch 14 includes a distal end portion 60. The side catheter branch 14 can be secured to the side balloon 28 at a side balloon connection point 62.

When the catheter assembly 10 is assembled prior to treatment of a vessel bifurcation 80, the stent 16 is operably mounted to the main balloon 26, the side inflation member 30, and the side catheter branch 14 as shown in FIG. 11. The distal end portion 60 of the side catheter branch 14 extends through a proximal open end 70 of the stent 16 and passes out of the stent 16 through a lateral branch opening 74 at a location along the stent 16 between proximal and distal ends 70, 72, thereof.

When using the catheter assembly 10 for treatment, the main and side catheter branches 12, 14 are advanced over main and branch guidewires 18, 20, respectively, to a vessel bifurcation 80. Typically, when catheter assembly 10 is used to treat a vessel bifurcation 80, the main catheter branch 12 remains in the main vessel 82 at an axial position that spans an opening into a branch vessel 84 (see FIG. 12). The distal end 60 of the side catheter branch 14 extends into the branch vessel 84. Positioning the distal end portion 60 in the branch vessel 84 can assist in aligning the lateral branch opening 74 of the stent 16 with the opening into the branch vessel 84 prior to and during expansion of the stent 16 within the main vessel 82.

The side balloon 28 is typically aligned radially and axially relative to the lateral branch opening 74 of the stent 16. The side balloon 28 is configured to extend radially outward relative to the main balloon 26 when the side balloon 28 is inflated. The side balloon 28, when inflated, typically expands an expandable portion 76 of the stent structure that defines the lateral branch opening 74. The expandable portion 76 moves in a radial outward direction relative to the main body of the stent and into the branch vessel 84 when the side balloon 28 is inflated (see FIG. 12).

In follow-up treatment steps the main and side catheter branches 12, 14 can be retracted distally from the stent 16 and a separate secondary balloon catheter can be advanced through a lateral branch opening and inflated to further expand the expandable portion 76 into engagement with the branch vessel 84. In a still further treatment step, a secondary stent can be advanced through the lateral branch opening 74 and expanded into engagement with the branch vessel 84 while overlapping at least a portion of the expandable portion 76 of stent 16.

Typically, the main and side balloons 26, 28 are coupled in fluid communication with a common inflation lumen that is defined in the catheter shaft 22. The common inflation lumen (labeled as main inflation 34 in at least FIG. 4) can be conventional, and extend distally from a distal end of the catheter assembly 10 that remains outside of the patient. The main inflation lumen 34 is used to supply pressurized inflation fluid to the main and side balloons 26, 28 during inflation and drain the inflation fluid when deflating the balloons 26, 28.

The balloons 26, 28 are shown connected in fluid communication in a series arrangement wherein fluid flows from the main inflation lumen 34, through the main balloon 26, and into the side balloon 28. This arrangement of the balloons 26, 28 can provide advantages and functionality that will be described in further detail below.

Referring now to FIGS. 1-6, further details related to the catheter assembly 10 are provided without inclusion of the stent 16 in the Figures. The main and side balloons 26, 28 are shown in an inflated state in FIGS. 1-5. The main balloon 26 includes a proximal balloon waist 38, a distal balloon waist 40, a tab 42 (see FIG. 6), and a guidewire housing bond 44. The tab 42 is defined by a pair of slits 43 formed in the distal balloon waist 40. The slits 43 can extend from a distal most point on the balloon 26 in a proximal direction a length L2. The length L2 can be less than a total length L1 of the distal balloon waist 40 (see FIG. 6). Alternatively, the length L2 can be equal to or greater than the length L1. The tab 42 is used to help in the arrangement of parts prior to forming the distal bond 32 between the side inflation member 30 and the main balloon 26 as will be described further below.

The side inflation member 30 includes a proximal end 46 and a distal end 48. The proximal end 46 can be secured to a distal side of the side balloon 28. The distal end 48 can be secured to the main balloon 26 at the distal bond 32. The side inflation member 30 is connected in fluid communication with the main balloon 26 such that inflation fluid flows from a main inflation lumen 34 defined in the catheter shaft 22 (see FIG. 4), through the main balloon 26, and into the side balloon 28. The side inflation member 30 does not, in this example, include a proximal segment that extends from the side balloon 28 in a proximal direction for connection at a location proximal of the side balloon 28 (e.g., a connection point at the proximal balloon waist 38 of the main balloon 26). Eliminating the proximal segment of the side inflation member 30 can reduce potential spatial interference with the side catheter branch 14 when trying to maintain alignment of the side catheter branch 14 along a central axis of the side balloon 28.

As shown in FIG. 2, the side catheter branch 14 can maintain alignment along a central, longitudinal axis of the side balloon 28 when there is no proximal segment of the side inflation member 30. Maintaining alignment of the side catheter branch 14 relative to the side balloon 28 can help maintain alignment of the side catheter branch 14 relative to the lateral branch opening 74 of the stent 16. Providing for consistent central alignment of the side catheter branch 14 with the side balloon 28 and lateral branch opening 74 can improve consistency in aligning the lateral branch opening 74 with the opening into a branch vessel 84 of a vessel bifurcation 80.

A side balloon connection point 62 can be provided to physically secure the side catheter branch 14 to the side balloon 28. In one example, the side balloon connection point 62 is located along a proximally facing side surface of the balloon 28. Typically, the side balloon connection point 62 is arranged along a central longitudinal axis Y (see FIG. 1) of the side balloon 28 that is also aligned along a longitudinal axis X of the main balloon 26 (see FIG. 2).

The side balloon connection point 62 can comprise any desired physical connection between the side catheter branch 14 and side balloon 28. In one example, the side balloon connection point 62 comprises a laser weld. In another example, the side balloon connection point 62 comprises an adhesive bond. Other types of connecting methods and structures are possible such as, for example, diode laser bonds, radiopaque marker crimping, and alternative thermal welding methods such as hot jaw welding, vibrational welding and ultrasonic welding.

In some examples, the side balloon connection point 62 is located on the side balloon 28 at a location that has sufficient material thickness and other material properties to minimize the chance of compromising the intended function and performance of the side balloon 28 as the side balloon 28 is inflated. The side balloon connection point 62 is constructed to withstand significant forces applied during inflation of the side balloon 28 to expand the expandable portion 76 of the stent 16 and any torque forces applied as the side catheter branch 14 is used to help align the lateral branch opening 74 of the stent 16 relative to the opening into the branch vessel 84 at the vessel bifurcation 80.

The connection point 62 can include additional material to help increase the bond tensile, radial and burst strength of the connection point 62. A sleeve (not shown) or other structure can be used as the source of additional material. The additional material can also be added in the form of beading that is added before creating the bond, or the addition of a sheet of material between the side inflation member 30 and the main catheter branch 12.

The distal bond 32 will now be described in further detail with reference to FIGS. 1-10. The distal bond 32 involves the connection between side inflation member 30 and the main balloon 26 at a location distal of the side balloon 28. As shown in FIG. 4, the distal bond 32 provides fluid communication between the main balloon 26 and the side inflation member 30 at a location along the distal balloon waist 40 of the main balloon 26. The distal bond 32 can be located in other arrangements at any location distal of the side balloon 26.

An example method of forming the distal bond 32 is described with reference to FIGS. 6-10. The main balloon 26 includes a tab 42 defined by a pair of slits 43 along the distal balloon waist 40. The distal bond 32 is formed by extending a main mandrel 56 through the distal balloon waist 40, and a side mandrel 58 through the side inflation member 30. A bond tube 50 is advanced over the main and side mandrels 56, 58 at a location distal of the side inflation member 30 and the distal balloon waist 40. The bond tube 50 has a flared proximal end portion 52, and a distal portion 54. The proximal end portion 52 is advanced over the distal end 48 of the side inflation member and advanced into the distal balloon waist 40 through the slits 43. Typically, the bond tube 50 is advanced proximally until reaching the proximal end of the slits 43 as shown in FIG. 8.

FIG. 10 is a cross-sectional view showing the arrangement of the mandrels 56, 58 relative to the side inflation member 30 and the distal balloon waist 40. FIG. 9 is a top view of the assembly shown in FIG. 8. With the bond tube 50 in position relative to the side inflation member and main balloon, heat is applied to the distal bond 32 to thermally bond the bond tube 50 to both the main distal balloon waist 40 and side inflation member 30. A thermal bond is created as the polymeric materials of each of the bond tube 50, side inflation member 30, and main balloon 26 flow together. The thermal bond can result in a relatively cohesive, integral joint between all three formerly independent pieces.

The main and side mandrels 56, 58 are typically coated with a substance such as Teflon so as to inhibit bonding of any of the pieces 40, 28, 50 with the mandrels 56, 58 during or after forming the distal bond 32. After the distal bond 32 has been generated, the mandrels 56, 58 are removed, the main guidewire housing 24 is extended through the distal balloon waist 40, and the distal balloon waist 40 is secured to the main guidewire housing 24 at a location distal of the distal bond 32 to form a guidewire housing bond 44. The resulting structure (shown in FIGS. 4 and 5) defines a fluid communication path between the main inflation lumen 34, the main balloon 26, the side inflation member 30, and the side balloon 28 with a fluid tight seal being provided between the main balloon 26 and the main guidewire housing 24 at the guidewire housing bond 44.

Other methods and configurations are possible for creating a distal bond between the side inflation member 30 and the main balloon 26 to provide fluid communication between the side inflation member 30 and the main balloon 26 at a location distal of the side balloon 26. The distal end 48 of the side inflation member 30 can be secured to the main balloon at a location proximal of the distal balloon waist 40 such as along any exterior surface of the main balloon 26 located distal of the side balloon 28. In one example, an aperture or hole is formed in a side wall of the main balloon 26 during manufacture of the main balloon to provide a fluid communication port to which the side inflation member 30 can be later connected in fluid communication. In another example, the side balloon 28 is secured to the main balloon at a location proximal of the distal balloon waist 40. In a yet further example, the distal bond can include a cone portion of the main balloon 26 at a proximal or distal end portion of the main balloon 26.

The Example of FIGS. 13 and 14

FIGS. 13 and 14 illustrate another example configuration for a side balloon 128. The side balloon 128 is connected to a side inflation member 30 at a proximal end 46 thereof. In contrast to the hemispherical-shaped side balloon 28 shown in FIGS. 1-12, the side balloon 128 extends longitudinally along the length of the side inflation member 30. FIG. 13 illustrates the side balloon 128 in a deflated state. FIG. 14 illustrates side balloon 128 in an inflated state extending in a direction perpendicular relative to a longitudinal axis of the side inflation member 30 to extend through a lateral branch opening 74 of the stent 16 when inflated.

The side balloon 28 can be formed using, for example, a vacuum molding process to create the side balloon 28 along the length of the side inflation member 30. After creation of the side balloon 128, a proximal segment of the side inflation member 30 can be removed and sealed closed at the proximal side of the side balloon 28. FIGS. 7 and 8 illustrate the side balloon 28 formed along the length of the side inflation member 30. After forming the distal bond 32, the proximal unused portion 49 can be removed so that it does not interfere with the alignment of the side catheter branch 14 with a central axis of the side balloon 28 when a catheter assembly 10 is assembled (see FIGS. 11 and 12).

Materials and Other Considerations

The materials used in the balloons and catheter shafts disclosed herein can be made of any suitable material including, for example, thermoplastic polymers, polyethylene (high density, low density, intermediate density, linear low density), various co-polymers and blends of polyethylene, ionomers, polyesters, polycarbonates, polyamides, poly-vinyl chloride, acrylonitrile-butadiene-styrene copolymers, polyether-polyester copolymers, and polyetherpolyamide copolymers. One suitable material is Surlyn®, a copolymer polyolefin material (DuPont de Nemours, Wilmington, Del.). Still further suitable materials include thermoplastic polymers and thermoset polymeric materials, poly(ethylene terephthalate) (commonly referred to as PET), thermoplastic polyamide, polyphenylene sulfides, polypropylene. Some other example materials include polyurethanes and block copolymers, such as polyamide-polyether block copolymers or amide-tetramethylene glycol copolymers. Additional examples include the PEBAX® (a polyamide/polyether/polyester block copolymer) family of polymers, e.g., PEBAX® 70D, 72D, 2533, 5533, 6333, 7033, or 7233 (available from Elf AtoChem, Philadelphia, Pa.). Other examples include nylons, such as aliphatic nylons, for example, Vestamid L21011F, Nylon 11 (Elf Atochem), Nylon 6 (Allied Signal), Nylon 6/10 (BASF), Nylon 6/12 (Ashley Polymers), or Nylon 12. Additional examples of nylons include aromatic nylons, such as Grivory (EMS) and Nylon MXD-6. Other nylons and/or combinations of nylons can also be used. Still further examples include polybutylene terephthalate (PBT), such as CELANEX® (available from Ticona, Summit, N.J.), polyester/ether block copolymers such as ARNITEL® (available from DSM, Erionspilla, Ind.), e.g., ARNITEL® EM740, aromatic amides such as Trogamid (PA6-3-T, Degussa), and thermoplastic elastomers such as HYTREL® (Dupont de Nemours, Wilmington, Del.). In some embodiments, the PEBAX®, HYTREL®, and ARNITEL® materials have a Shore D hardness of about 45D to about 82D. The balloon materials can be used pure or as blends. For example, a blend may include a PBT and one or more PBT thermoplastic elastomers, such as RITEFLEX® (available from Ticona), ARNITEL®, or HYTREL®, or polyethylene terephthalate (PET) and a thermoplastic elastomer, such as a PBT thermoplastic elastomer. Additional examples of balloon material can be found in U.S. Pat. No. 6,146,356. It should be understood that the specific materials disclosed below for the individual embodiments does not limit the embodiment to those materials.

In the example catheter assemblies described above, some of the features can include a lubricious coating on an exterior surface thereof. The coating can promote insertion of the branch balloon into the branch vessel of a vessel bifurcation. The coating can also improve removal of the branch balloon from the branch vessel and the branch aperture of the stent when deflating and removing the catheter assembly from the vessel bifurcation after expansion of the stent. Some example coating for use with the branch balloon include hydrophilic polymers such as polyarylene oxides, polyvinylpyrolidones, polyvinylalcohols, hydroxyl alkyl cellulosics, algins, saccharides, caprolactones, and the like, and mixtures and combinations thereof. Hydrophilic polymers can be blended among themselves or with formulated amounts of water insoluble compounds (including some polymers) to yield coating with suitable lubricity, bonding and solubility. In some examples, portions of the devices described herein can be coated with a hydrophilic polymer or a fluoropolymer such as polytetrafluoroethylene (PTFE), better known as TEFLON®.

While the example stent delivery systems described above illustrate a balloon expandable stent having a predetermined side opening (i.e., branch aperture), other types of stents can be used with the catheter features described above. A variety of stents can be used with the systems and methods disclosed herein. Examples of such stents can be found in, for example, in U.S. Pat. Nos. 6,210,429; 6,325,826; and 7,220,275, the entire contents of which are incorporated herein by reference. In general, the aforementioned stents have a tubular shape with a continuous sidewall that extends between the proximal and distal ends. Proximal and distal stent apertures are defined at respective proximal and distal ends of the stent. A branch aperture is defined in the sidewall of the stent. The branch aperture provides access between an interior of the stent and an exterior of the stent. In some stents, the branch aperture includes expandable structure around a peripheral edge thereof that expands in a generally radial outward direction relative to a longitudinal axis of the stent. The expandable structure can be configured to extend into the branch lumen of the bifurcation upon expansion of the stent. The stent includes a plurality of strut structures that define the sidewall. The struts are expandable from a first, unexpanded state to a second, expanded state. Typically, the stent is configured to maintain the expanded state. The struts define a plurality of cell openings or cells along a length of the stent. The size and shape of the cells is typically different than the size and shape of the branch aperture. The stent is typically expanded once the stent is properly positioned in the main lumen of the bifurcation with the branch aperture aligned radially and axially with an opening into the branch lumen. The stent, including the expandable structure surrounding the branch aperture, can be expanded with a single expansion or with multiple expansions using, for example, one or more inflatable balloons.

CONCLUSION

One aspect of the present disclosure relates to a catheter assembly that includes a main catheter branch having a catheter shaft, a main balloon, a main guidewire housing, and a side balloon assembly. The catheter shaft has a distal end portion and defines an inflation lumen. The main balloon is positioned at the distal end portion of the catheter shaft. The main balloon has a distal waist portion. The main guidewire housing defines a main guidewire lumen. The side balloon assembly includes a side balloon and a side inflation member. The side inflation member has a distal end portion and a proximal end portion. The side balloon is positioned at the proximal end portion of the side inflation member and in fluid communication with the side inflation member. The distal end portion of the side inflation member is secured in fluid communication with the main balloon at the distal waist portion of the main balloon.

Another aspect of the present disclosure relates to a stent delivery system, that includes a stent and a first catheter branch. The stent has a distal open end, a proximal open end, and a side branch aperture. The side branch aperture is defined in the stent at a location positioned between the distal and proximal open ends. The first catheter branch includes a catheter shaft, a main balloon, a guidewire housing, and a side balloon assembly. The catheter shaft has a distal end portion and defines an inflation lumen. The main balloon is positioned at the distal end portion of the catheter shaft and has a proximal end portion and a distal end portion. The main balloon extends within the stent from at least the proximal open end to the distal open end of the stent. The guidewire housing extends through the main balloon from the proximal end portion to the distal end portion, and defines a main guidewire lumen. The side balloon assembly includes a side balloon and a side inflation member. The side inflation member has a proximal end portion that is connected in fluid communication with the side balloon, and a distal end portion that is connected in fluid communication with the main balloon at a location distal of the side balloon. The side balloon is positioned in axial and radial alignment with the side branch aperture of the stent.

Another aspect of the present disclosure relates to a method of expanding a stent with a catheter assembly. The catheter assembly includes a main catheter branch, a side catheter branch, and a side balloon assembly, the main catheter branch includes a main balloon and a catheter shaft. The catheter shaft defines a main inflation lumen. The main balloon is positioned on the catheter shaft. The side balloon assembly includes a side balloon and a side inflation member, wherein a distal end portion of the side inflation member is connected in fluid communication with the main balloon at a location distal of the side balloon. The stent includes a distal open end, a proximal open end, and a lateral branch aperture. The method includes steps of extending the main balloon extending through the stent from at least the proximal open end to the distal open end of the stent, positioning the side balloon within the stent in radial and axial alignment with the side branch aperture of the stent, extending the side catheter branch through the proximal open end of the stent and out of the lateral branch aperture of the stent, and inflating the main and side balloons to expand the stent.

The above specification, examples and data provide a complete description of the manufacture and use of the composition of the invention. Since many embodiments of the invention can be made without departing from the spirit and scope of the invention, the invention resides in the claims hereinafter appended.

We claim:

1. A catheter assembly, comprising:
 (a) a main catheter branch comprising:
  i. a catheter shaft, the catheter shaft having a distal end portion and defining an inflation lumen;
  ii. a main balloon positioned at the distal end portion of the catheter shaft, the main balloon having a distal waist portion; the main balloon having a proximal end portion and a distal end portion; wherein the main balloon includes the distal waist portion at the distal end portion
  iii. a main guidewire housing, the main guidewire housing defining a main guidewire lumen; and
  iv. a side balloon assembly, the side balloon assembly including:
   A. a side balloon; and
   B. a side inflation member, the side inflation member having a proximal end portion connected in fluid communication with the distal end of the side balloon, and a distal end portion connected in fluid communication with the main balloon at a location distal of the side balloon, wherein the side inflation member does not include a proximal end segment that extends from the side balloon in a proximal direction.

2. The catheter assembly of claim 1, further comprising a side catheter branch, the side catheter branch defining a branch guidewire lumen.

3. The catheter assembly of claim 2, wherein the side catheter branch is operatively connected to the side balloon assembly.

4. The catheter assembly of claim 2, wherein side catheter branch is aligned with a longitudinal axis of the side balloon.

5. The catheter assembly of claim 3, wherein the side catheter branch is connected to the side balloon at a side balloon connection point.

6. The catheter assembly of claim 1, wherein the side inflation member is secured to the main balloon at a distal bond, the distal bond including a connection between a bond tube member, the distal waist portion of the main balloon, and the distal end portion of the side inflation lumen.

7. The catheter assembly of claim 1, wherein the side balloon assembly terminates at a location distal of a proximal waist portion of the main balloon.

8. The catheter assembly of claim 7, wherein the side balloon assembly terminates at a location adjacent to a proximal side surface of the side balloon.

9. The catheter assembly of claim 1, wherein the distal waist portion of the main balloon includes a tab member, the tab member being defined by at least one slit formed in the distal waist portion of the main balloon that extends longitudinally.

10. A stent delivery system, comprising:
 (a) a stent, the stent having a distal open end, a proximal open end, and a side branch aperture, the side branch aperture defined in the stent at a location positioned between the distal and proximal open ends; and
 (b) a first catheter branch, the first catheter branch comprising:
  i. a catheter shaft, the catheter shaft having a distal end portion and defining an inflation lumen;
  ii. a main balloon positioned at the distal end portion of the catheter shaft, the main balloon having a proximal end portion and a distal end portion, the main balloon extending within the stent from at least the proximal open end to the distal open end of the stent;
  iii. a guidewire housing extending through the main balloon from the proximal end portion to the distal end portion, the guidewire housing defining a main guidewire lumen; and
  iv. a side balloon assembly, the side balloon assembly including:
   A. a side balloon having a proximal end and a distal end; and B. a side inflation member, the side inflation member having a proximal end portion connected in fluid communication with the distal end of the side balloon, and a distal end portion connected in fluid communication with the main balloon at a location distal of the side balloon, the side balloon being positioned in axial and radial alignment with the side branch aperture of the stent, wherein the side inflation member does not include a proximal end segment that extends from the side balloon in a proximal direction.

11. The stent delivery system of claim 10, further comprising a side catheter branch, the side catheter branch including a distal end portion and defining a branch guidewire lumen, the distal end portion of the side catheter branch extending into the stent through the proximal open end of the stent and extending out of the stent through the side branch aperture.

12. The stent delivery system of claim 11, wherein the side catheter branch is operatively connected to the side balloon assembly.

13. The stent delivery system of claim 12, wherein the side catheter branch is connected to the side balloon at a side balloon connection point.

14. The stent delivery system of claim 10, wherein the connection between the distal end portion of the side inflation member and the main balloon is a distal bond positioned at the distal end portion of the main balloon.

15. The stent delivery system of claim 14, wherein the distal bond includes a thermal bond between the side inflation member, the distal end portion of the main balloon, and a bond tube that extends over at least a portion of the distal end portion of the side inflation member and within at least a portion of the distal end portion of the main balloon.

16. The stent delivery system of claim 10, wherein the main balloon includes a distal waist portion at the distal end portion of the main balloon, and the side inflation member is connected in fluid communication with the main balloon at the distal waist portion.

* * * * *